United States Patent [19]

Bauer et al.

[11] Patent Number: 4,810,633
[45] Date of Patent: Mar. 7, 1989

[54] ENZYMATIC ETHANOL TEST

[75] Inventors: Robert Bauer, Bristol; Thomas A. Magers, South Bend, both of Ind.

[73] Assignee: Miles Inc., Elkhart, Ind.

[21] Appl. No.: 616,732

[22] Filed: Jun. 4, 1984

[51] Int. Cl.$^4$ .............. C12Q 1/26; C12Q 1/28; C12N 9/96
[52] U.S. Cl. .................. 435/25; 435/28; 435/805; 435/188; 427/2
[58] Field of Search ........... 422/56, 57; 435/4, 25, 435/28, 188, 805, 810; 427/2

[56] References Cited

U.S. PATENT DOCUMENTS

| | | | |
|---|---|---|---|
| 3,413,198 | 11/1968 | Deutsch | 435/4 X |
| 3,630,957 | 12/1971 | Rey et al. | 435/14 X |
| 3,721,607 | 3/1973 | Gruber et al. | 435/28 |
| 3,862,885 | 1/1975 | Kano et al. | 435/28 |
| 3,926,736 | 12/1975 | Bucolo | 435/26 |
| 3,979,262 | 9/1976 | Hunziker | 435/28 |
| 4,250,261 | 2/1981 | Eggeling et al. | 435/190 |
| 4,312,834 | 1/1982 | Vogel et al. | 422/56 |
| 4,363,634 | 12/1982 | Schall, Jr. | 422/57 X |
| 4,385,114 | 5/1983 | Güthlein et al. | 435/28 |
| 4,427,770 | 1/1984 | Chen et al. | 435/14 |
| 4,430,427 | 2/1984 | Hopkins | 435/25 |
| 4,438,067 | 3/1984 | Siddiqi | 422/56 |
| 4,451,569 | 5/1984 | Kobayashi et al. | 435/188 |
| 4,492,754 | 1/1985 | Träger et al. | 435/28 |
| 4,642,286 | 2/1987 | Moldowan | 435/28 |

FOREIGN PATENT DOCUMENTS

| | | | |
|---|---|---|---|
| 3124590 | 1/1983 | Fed. Rep. of Germany | 435/28 |
| 0045198 | 4/1981 | Japan | 435/28 |
| 0068788 | 4/1982 | Japan | 435/188 |

OTHER PUBLICATIONS

Janssen et al., "Biochimica et Biophysica Acta", 151, (1968), pp. 330-342.
Majkic-Singh, "Analytica Chimica Acta", 115, (1980), pp. 401-405.
Hunting et al., "Analytical Chemistry", 31(1), (1959), pp. 143-144.
"Biochemicals Technical Information Bulletin: Alcohol Oxidase", Phillips Chemical Co., Bulletin #23785e, (1985).
Dubowski, "Laboratory Mgt.", (Apr. 1982), pp. 27-29 and 33-36.
Chaudhary et al., "J. Clin. Pathology 36", (10), (1983), pp. 1201-1202.

*Primary Examiner*—Esther M. Kepplinger
*Attorney, Agent, or Firm*—Roger N. Coe

[57] ABSTRACT

The present invention provides a stable, convenient solid state test device for the determination of ethanol in an aqueous test sample, a method for its preparation and a method for its use. The use of carrier matrix incorporated with alcohol oxidase, a peroxidatively active substance and a suitable chromogenic indicator for the determination of ethanol in aqueous samples such as body fluid samples (e.g., serum, urine or saliva) is part of the invention. The invention provides a method of incorporating the enzyme alcohol oxidase and a peroxidatively active substance into a carrier matrix with a chromogenic indicator system capable of providing a detectable response to the presence of at least 100 mg/dL ethanol in less than about 5 minutes. The method involves either (a) the use of a specialized incorporation procedure or (b) the addition of an azide to the test device. Either method overcomes the "false positive" problem seen when solution assay reagents are incorporated at the increased concentrations necessary to provide a test device sensitive to the at least 100 mg/dL ethanol.

6 Claims, No Drawings

ENZYMATIC ETHANOL TEST

FIELD OF THE INVENTION

The invention relates generally to the determination of an analyte in an aqueous test sample with a solid state reagent strip (test device). In particular, the invention relates to a solid state test device useful for the determination of ethanol in an aqueous test sample. Of particular interest are body fluid samples such as blood, urine or saliva.

UTILITY

Ethanol testing is useful industrially, medically and for law enforcement. Industrially, the level of ethanol present can be used to determine the progress of fermentation or of solvent purification. In addition, alcoholic beverages and medicinals must be tested to determine if the desired level of ethanol is present. Medically, the presence and level of ethanol in the blood stream can be used to aid differential diagnosis among possible origins of loss of motor function or life threatening coma. The determination of blood ethanol could also be used as an aid in compliance programs for problem drinkers and for those diagnosed as alcoholics. Legally, the level of ethanol in the blood stream is used as an objective indicium of fitness to operate machinary or to drive an automobile or other vehicles. A simple, fast, convenient method of determining the blood alcohol is particularly important for law enforcement.

INFORMATION DISCLOSURE

1. Ethanol Assays

Given the importance and wide ranging utility for ethanol testing, it is not surprising that many assay methods are available. Ethanol testing can be accomplished instrumentally by potentiometric measurement, by infrared spectroscopy or by gas chromatography. In addition, both enzymatic and nonenzymatic solution assays are available. Nonenzymatic assays use strong oxidizing agents such as permanganate and dichromate which change color when they react with ethanol. Unfortunately, due to their nonspecific nature they also react with many other oxidizable substances causing erroneously high results. Enzymatic assays are generally based on the use of alcohol dehydrogenase or alcohol oxidase. These assays often also utilize a competitive inhibitor of the enzyme to facilitate quantitative determination of an analyte. (See, for example, U.S. Pat. No. 3,977,944.)

The enzymatic action of alcohol dehydrogenase (ADH) on ethanol proceeds as follows:

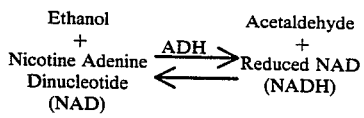

The reduced nicotine adenine dinucleotide (NADH) can then be determined directly by ultraviolet spectroscopy or the above reaction can be coupled with a second enzymatic reaction which allows the conversion of ethanol to NADH to be followed in the visible region of the spectrum.

Since the equilibrium of the above reaction lies strongly toward ethanol, an acetaldehyde-trapping agent is often used as a means to drive the reaction toward the production of NADH. (See, for example, U.S. Pat. No. 3,926,736.) "Alcohol Analysis: Clinical Laboratory Aspects, Part II", K. M. Dubowski, Laboratory Management, April 1982, p. 33, provides a table on the major features of enzymatic (ADH) oxidation methods for blood-alcohol determination. The table discloses that assays based on the foregoing reaction can be facilitated by the use of semicarbizide as an acetaldehyde-trapping agent. The NADH produced can then be determined by the use of diaphorase and iodonitrotetrazolium chloride to form a colored end product (formazan).

Other methods have been found to obviate the need for an acetaldehyde-trapping agent. G.B. Pat. No. 1,351,547 describes a method which comprises testing a sample with an aqueous solution of alcohol dehydrogenase and a specified tetrazolium salt in amounts which provide a quantitative colorimetric response when in contact with the sample, NAD, diaphorase, and a buffer. The patent discloses a stable lyophilized composition of alcohol dehydrogenase and tetrazolium salt and indicates that additional components, such as albumin or gelatin and an antioxidant (e.g., a reduced mercaptan), will further stabilize the reaction so that an acetaldehyde-trapping agent is no required.

The other enzymatic pathway utilizes alcohol oxidase (AOD) and proceeds as follows:

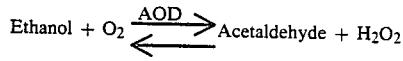

This reaction can be coupled with a second enzymatic reaction which allows the determination of hydrogen peroxide in the visible region of the spectrum by the addition of peroxidase and a chromogenic indicator. This series of liquid reactions, used for the assay of alcohol oxidase, has been published by Phillips Chemical Co. in a Biochemicals Technical Information Bulletin on Alcohol Oxidase (23785E).

In U.S. Pat. No. 4,430,427 the sodium azide inhibition of the rate of methanol conversion by alcohol oxidase was measured by following the oxygen consumption in solution with a dissolved oxygen probe. The patent describes the formation of a red absorbing combination when an azide is added to an alcohol oxidase preparation.

2. Reagent Strip Format

It has been suggested that the solution assay composition for the determination of alcohol dehydrogenase can be incorporated onto solid state test devices. See, for example, U.S. Pat. No. 4,394,444, commonly assigned to the present assignee, which describes an analyte determination wherein the analyte reacts with a dehydrogenase, such as alcohol dehydrogenase, to produce NADH. The NADH is then determined with an uncoupler and peroxidase to produce color. The patent suggests that a system can be incorporated into a solid state test device. However, there is no published information of which the inventors are aware on how to incorporate an alcohol oxidase solution assay into a test device.

SUMMARY OF THE INVENTION

The present invention provides a test device for the determination of ethanol in an aqueous test sample, a method for its preparation and a method for its use. The test device is composed of a carrier matrix incorporated with alcohol oxidase, a peroxidatively active substance and a chromogenic indicator system capable of providing a detectable colorimetric response, wherein the chromogenic indicator system is substantially in the reduced (uncolored) form and the alcohol oxidase is present in a quantity sufficient to provide a colorimetric response to at least 100 mg/dL ethanol in less than 5 minutes. When azide is additionally incorporated, the device can be used to quantitatively determine ethanol content. The use of alcohol oxidase, a peroxidatively active substance and a suitable chromogenic indicator incorporated into a carrier matrix for determining ethanol in an aqueous test sample is also considered to be part of the invention.

In use, the aqueous test sample is contacted with the test device. The presence of 100 mg/dL ethanol and/or concentration of ethanol in the test sample is then determined by observing any detectable colorimetric response produced in less than about 5 minutes.

The test device of the present invention overcomes the false positive problem seen when increased concentrations of solution assay components, used to provide sufficient sensitivity to detect at least 100 mg/dL ethanol in an aqueous test sample, are simply incorporated into a carrier matrix. The test device provides rapid results, sufficient detectable response forming in less than 5 minutes. The device can be prepared with ordinary drying techniques and does not require lyophilization.

DETAILED DESCRIPTION OF THE INVENTION

Solution assay reagent concentrations are usually too low to provide a sensitive assay when incorporated into a solid state test device. Therefore, a reagent concentrations incorporated into a carrier matrix must be increased and of course the concentrations in the final dry solid state test device are even higher. This concentration change itself often leads to peculiar problems related to differences in interactions and stabilities of the components in the solid state test device. These problems are particularly egregious when enzymes are involved.

In the case of an alcohol oxidase based ethanol test, direct incorporation of the solution assay reagent concentrations into a carrier matrix does not produce a test device with satisfactory sensitivity. Required sensitivity can vary with the intended use of the test device. For compliance programs, very low levels of blood ethanol—25 to 50 mg/dl (milligrams per deciliter)—would indicate noncompliance. For law enforcement, test must be sensitive to the legally set limit, which in the United States is usually about 100 mg/dL blood ethanol. The experimental protocols used herein required sensitivity to at least 100 mg/dL ethanol in an aqueous fluid sample with a colorimetric response in less than about 5 minutes. A preferred test device can indicate the presence of 100 mg/dL ethanol in about 1 to 2 minutes, most preferably 1 minute or less.

When solution assay reagent concentrations are increased to provide the requisite sensitivity as defined above, incorporated into a carrier matrix and dried, the indicator is substantially in the oxidized form (i.e., colored) even prior to contact with an aqueous test sample containing ethanol. In other words, a test device so prepared gives an instantaneous and ubiquitous false positive test for ethanol. While false positives are always undesirable, they are particularly detrimental in ethanol testing. False indications of noncompliance could seriously damage a program's ability to rehabilitate problem drinkers. Of course, a false positive test indicating a blood alcohol level over the legal limit would have a particularly serious consequences for a driver.

The false positive problem is either not seen in the dilute solution assay or is perhaps negated by the use of a blank (i.e., comparison with an unreacted portion of the test composition). The problem also appears to be unique to alcohol oxidase since other oxidase enzymes such as glucose oxidase, cholesterol oxidase, uricase and galactose oxidase, used in the high concentrations required to produce a sensitive dry solid state test device, do not exhibit this high degree of false positive response.

The present invention solves the false positive problem seen in the reagent strip format, either by the use of a specialized incorporated procedure or by the addition of an azide to the test composition.

The present inventors speculate, but do not base their invention on, the premise that the unbiquity of low molecular weight primary alcohols in reagents used may contribute to the false positive problem. In addition, there is some evidence that alcohol oxidase may react with the primary hydroxy groups of serine residues on the enzyme itself, an autooxidation process unknown in other oxidase enzymes.

Two approaches have been used to obviate the false positive problem seen when the solution assay composition, in increases concentration levels, is incorporated into a carrier matrix to produce a solid state test device. One approach is used when the chromogenic indicator system is composed of a coupled pair of indicator components. In that case, one component is incorporated into the carrier matrix with the peroxidatively active substance and alcohol oxidase, and the impregnated carrier is dried prior to the incorporation of the second chromogenic component.

A second approach to eliminating the false positive problem is the addition of an azide, such as sodium azide. While the azide performs as a competitive inhibitor, allowing the quantitative assay of ethanol at high concentrations, it is speculated that it also protects the enzyme from its self-destructive tendencies, which tendencies may contribute to the false positive problem. The addition of azide is the best mode known to the inventors for producing a solid state test device which is sensitive to at least 100 mg/dL ethanol and yet the chromatogenic component of an indicator system is substantially in the reduced form (i.e., no false positive reaction). The addition of azide is preferable even when specialized incorporation techniques are utilized.

A. Test Components

Preparations exhibiting alcohol oxidase activity are available from a variety of sources including species of fungae and yeasts. Preparations from Pichia-Type yeasts are a preferred source of alcohol oxidase. Such yeast sources are listed in U.S. Pat. No. 4,430,427 incorporated herein by reference. The alcohol oxidase preparations used react with ethanol and other lower primary alcohols, such as methanol and 1-propanol.

Peroxidatively active substances, useful in the present invention, can be chosen from various organic and inorganic sources. Plant peroxidases, such as horseradish peroxidase or potato peroxidase, can be used. In addition, even though less satisfactory, hemin and hemin derivatives, hemoglobins and hematin can be used.

The chromogenic indicator system can be either a single component or two components forming a coupled chromogenic indicator system. A single chromogenic component, such as 3,3', 5,5'-tetramethylbenzidine, o-tolidine, guaic and mixtures thereof as well as 2-amino-8-naphthol-3,6-disulfonic acid, or p-anisidine. When a single chromogenic component is used, an azide is preferably included in the test composition to obviate the false positive problem. 3,3',5,5'-Tetramethylbenzidine, o-tolidine and gum guaic are preferred single chromogenic indicator components. Coupled chromogenic components, such as 3,5-dichloro-2-hydroxybenzene sulfonic acid (DHSA)/4-aminoanipyrine, 3,5-dichloro-2-hydroxybenzene sulfonic acid/3-methyl-2-benzothiazoline hydrazone or m-anisidine/4-aminoantipyrine, or mixtures thereof among others, can be used to prepare the test device. The chromogenic pair, DHSA/4-aminotantipyrine is a preferred coupled indicator system.

Choice of the chromogenic indicator system can affect the ability of the test device to fulfill the stated criteria of providing a colorimetric response to the presence of 100 mg/dL ethanol in an aqueous test sample in less than about 5 minutes. Given the present disclosure, choice of a sufficiently sensitive indicator system can be made by one of ordinary skill in the art.

Preferred azides are the metal salt azides, particularly the electropositive metal azides which are not explosive. Particularly preferred are the metal azides selected from the Group 1A of the Periodic Table according to Mendeleeff, such as lithium azide, sodium azide, potassium azide and the like. Of these sodium azide was found to be the most readily available commercially.

The pH optimum of alcohol oxidase is around pH 7.5. Therefore, although not required for all aqueous test samples, a buffer is prefeably incorporated into the test device. This is especially true if the test device is formulated for use with a body fluid such as urine where the pH of the sample may be as low as 4 to 5. Any buffer capable of providing a pH in the range of 5.0 to 9.0 can be used in the invention. Useful buffers include sodium phosphate, sodium citrate and tris(hydroxymethyl)aminomethane and tris(hydroxymethyl)-aminomethane glutamate. Other buffers can readily be chosen by those of ordinary skill in the art, given the present disclosure.

Additional components, such as wetting substances and color or shelf-life stabilizers, can be included as long as they do not interfere with the enzymatic reaction of alcohol oxidase with ethanol or that of the peroxidatively active substance with the generated peroxide. Suitable wetting substances includes polymers, such as polyvinyl pyrrolidone, and surfactants. A polyethoxylated fatty alcohol (obtained under the trademark Emulphor® ON 870 from GAF, New York, NY) can also be used. Dioctyl sodium sulfosuccinate (obtained under the trademark Aerosol® OT from Aldrich Chemical Co., Milwaukee, Wis.) acts as a surfactant and as a color stabilizer. Useful shelf-life stabilizers include sorbitol and tris(hydroxymethyl)aminomethane glutamate; sorbitol is particularly preferred.

The carrier matrix can be any substance capable of being incorporated with the components of the test composition. Thus, the matrix can take on many known forms, such as those utilized for reagent strips for solution analysis. For example, U.S. Pat. No. 3,846,247 teaches the use of felt, porous ceramic strips and woven or matted glass fibers. As substitutes for paper, U.S. Pat. No. 3,522,928 teaches the use of wood sticks, cloth, sponge material and argillaceous substances. French Pat. No. 2,170,397 teaches the use of carrier matrices having greater than 50% polyamide fibers therein. Another approach to carrier matrices is disclosed in U.S. Pat. No. 4,046,513, wherein the concept of printing reagents onto a suitable carrier matrix is employed. U.S. Pat. No. 4,046,514 discloses the interweaving or knitting of filaments bearing reagents in a reactant system.

It is, therefore, to be appreciated that in producing a test device of the invention all such carrier matrix concepts can be employed, as can others. The matrix can include a system which physically entraps any or all of these ingredients, such as polymeric microcapsules which rupture upon contact with an aqueous solution. For example, alcohol oxidase and the chromogenic indicator system or one component of a coupled chromogenic indicator, can be maintained separaely within the same carrier matrix without interaction until contacted with a solution. The matrix can also comprise a system wherein the composition ingredients are homogeneously combined in a fluid or semifluid state, which later hardens or sets, thereby incorporating the ingredients. Other matrix formats are contemplated, including the use of a microporous membrane or polymer film matrices. Microporous membranes are available as preformed membranes or can be prepared by such techniques as phase inversion. Suitable polymer films can be produced with commercially available latex formulations based on latex polymer suspensions such as those formed from a 60:40 copolymer of styrene and butadiene. Other natural or synthetic polymers or mixtures thereof can also be used. Examples of such film formulations can be found in U.S. Pat. Nos. 3,630,957 and 4,312,834, incorporated herein by reference.

The presently preferred method is to impregnate a bibulous carrier matrix, for example filter paper, with the composition followed by affixing the impregnated matrix to a support member. When a whole blood sample is tested, the impregnated carrier matrix can be coated to allow excess sample to be washed or wiped off.

B. Method of Preparation

Preferably, the reagent test strip or test device is prepared by sequential incorporation of the carrier matrix with drying between incorporation steps. Drying can be accomplished by any means which will not deletriously affect the incorporated composition, usually by means of an air oven. The dried paper can thereafter be cut and mounted on one end of a support member, for example, a rigid or semi-rigid polystyrene film strip. Mounting of the paper on the strip can be accomplished through use of a double-faced adhesive tape, such as that commercially available from the 3M Co. as DOUBLE STICK®.

The following examples illustrate the preferred methods of incorporation by (a) incorporating any organic soluble single chromogenic component prior to incorporation of alcohol oxidase and any remaining components, and drying thoroughly, (b) incorporating one component of a coupled chromogenic indicator into the carrier matrix with the alcohol oxidase with drying prior to the incorporation of the second chromogenic component or (c) incorporating a dried microporous polymer film containing alcohol oxidase and peroxidase with a chromogenic indicator. When split incorporation is used, the test strip can exhibit a slight coloration visibly different from the white of a paper carrier matrix. This coloration may intensify slightly when contacted with water. However, the chromogenic components remain substantially in the reduced (uncolored) form and there is a significant change in color in less than about 5 minutes when the device is contacted with an aqueous sample containing 100 mg/dL ethanol. Due to this slight coloration, however, it is preferred to incorporate an azide with the alcohol oxidase even when the coupled chromogenic components are split for incorporation.

The test device could also be prepared by combining the assay ingredients in a polymer matrix in a fluid or semi-fluid state and applying to a support. Examples of such procedures are also provided.

Incorporation can be accomplished by any method such as dipping, spreading or spraying which allows the carrier matrix to be substantially uniformly incorporated with the assay composition.

C. Concentration Ranges of Test Components

The concentration ranges of the test components are substantially higher than the concentrations required for solution assays of ethanol. The choice of appropriate concentrations is further complicated by the apparent interaction of azide with peroxidase ["Deleterious Effect of Sodium Azide on Activity of Peroxidase", 36 J. Clin. Pathology 10, 1983], as well as with alcohol oxidase (U.S. Pat. No. 4,430,427). In addition, appropriate concentrations very slightly depending on whether the test sample is urine, saliva, or blood. Preferably the required concentration of alcohol oxidase (AOD), which with the indicator system of choice can provide a sufficiently sensitive ethanol test, is determined first. The concentration of alcohol oxidase required is inversely related to the sensitivity of the indicator. An excess of peroxidase is used and preferably the ratio of azide to peroxidase (POD) is no more than 0.4:1 by weight, an amount which is sufficient to prevent a false positive indication without inhibiting the necessary activity of peroxidase.

The following table provides a guide to the working and preferred concentration ranges for components in the reagent solution used to prepare the test device of the present invention with the sensitivity and reaction time stated previiously. (Definition of units can be found under the heading "Examples").

|  | working | preferred |
| --- | --- | --- |
| saliva or serum | | |
| AOD | 10–250 IU/mL | 20–100 IU/mL |
| POD | 24–3600 IU/mL | 50–200 IU/mL |
| azide | 0 mM to 15 mM | 2.5 mM to 5 mM |
| urine | | |
| AOD | 10–500 IU/mL | 20–200 IU/mL |
| POD | 24–3600 IU/mL | 50–200 IU/mL |
| azide | 0 mM to 5.0 mM | 0.5 mM to 3.0 mM |

Most preferably the concentration of alcohol oxidase for a saliva/serum test device is 40 to 70 IU/mL and for urine is 50–150 IU/mL. In any case, the concentration of the single chromogenic component or each of the couple chromogenic components will be about 0.01 to 0.2M (molar), preferably about 0.025 to 0.1M. The buffer should provide a pH of from about 5 to 9, preferably from about 7 to 8. These concentrations ranges and relative concentrations of components are viable whether the solution is an aqueous impregnating solution or a polymer suspension.

D. Method of Use

The test device is advantageously used by momentarily dipping it in a test sample or by otherwise introducing a test sample onto the carrier matrix, whereby a detectable colorimetric change results when 100 mg/dL ethanol is present. Contact with the test sample can also be made by pipette, swab or spatula. Although dipping is a highly satisfactory method of contact when urine is used, a blood sample will normally require pipetting and the latter methods can be useful in testing saliva.

The following examples describe experiments which were performed in developing the present invention. While the examples serve to illustrate the invention, they are not to be interpreted as limiting its scope which is defined solefly by the claims appended hereto. One skilled in the art will be able to make such variations, substitutions and changes in the components of the composition and ingredients and reaction parameters as may be seem desirable.

EXAMPLES

Alcohol oxidase (AOD, EC 1.1.3.13) was obtained from Phillips Chemical Co., Bartlesville, OK. The activity of the alcohol oxidase used is given in International Units per milliliter (IU/mL) of stock solution. One Intermational Unit (IU) of activity catalyzes the formation of 1 micromole aldehyde and hydrogen peroxide in an air-saturated solution at pH 7.5, 25° C. The peroxidase used was horseradish peroxidase obtained from Miles Laboratories, Inc., Kankakee, Ill.. With an activity of 130 IU/mg.

Aerosol ® OT is the trademark used by Aldrich Chemical Co., Milwaukee WI, for dioctyl sodium sulfosuccinate. Emulphor ® ON 870 is the trademark used by GAF, New York, NY. The other reagents used are commercially available.

The following abbreviations are used in the examples:

| dL | deciliter |
| --- | --- |
| mL | milliliters |
| M | molar |
| mM | millimolar |
| °C. | degrees centigrade |
| mg | milligrams |
| IU | International Unit |
| TMB | 3,3',5,5'-tetramethylbenzidine |
| DHSA | 3,5-dichloro-2-hydroxybenzene sulfonic acid |
| MBTH | 3-methyl-2-benzothiazoline hydrazone |
| POD | peroxidase |
| AOD | alcohol oxidase |

Percentages used indicate weight in milligrams per 100 militers of aqueous solution (%w/v) unless otherwise indicated.

A. Direct Incorporation Solution Chemistry

Attempts were made to incorporate the solution assay for ethanol, described by Phillips Chemical Co. in a Biochemicals Technical Bulletin on Alcohol Oxidase, into a solid state test device. The assay follows the production of peroxide with an indicator system comprising a chromogenic indicator and peroxidase.

Whatman 3 MM filter paper was dipped into a solution using enzyme concentrations comparable to those used in the Phillips assay (i.e., 5 IU/mL alcohol oxidase in the impregnating solution) and dried 10 minutes at 60° C. in an air oven.

| solution | |
|---|---|
| o-dianisidine.2HCl (0.008% in 0.1 M phosphate buffer, pH 7.5) | 10 mL |
| POD, 12 mg/mL | 0.004 mL |
| AOD (500 IU/mL) | 0.1 mL |

The carrier so incorporated was white in color. However, when contacted with an aqueous test sample containing 100 mg/dL ethanol, there was no apparent color development, i.e., the test device produced by direct incorporation of the liquid assay reagents was not sufficiently sensitive to ethanol to produce a useful test device.

A second attempt was made to produce a test device based on the liquid assay of Phillips by increasing the concentrations of the enzymes to provide a more sensitive test. Whatman 3 MM filter paper was dipped in a solution containing about 10 times the concentration of alcohol oxidase and 100 times the concentration peroxidase used previously and and dried 10 minutes at 60° C. in an air oven.

| solution: | |
|---|---|
| o-dianisidine-2HCl (0.008% in 0.1 M phosphate, pH 7.5) | 8.5 ml |
| POD, 12 mg/mL | 0.5 ml |
| AOD (500 IU/mL) | 1.0 ml |

The dried carrier matrix developed a pale pink when contacted with either a blank (water only) or an aqueous test sample containing 100 mg/dL ethanol. There was very little differentiation between the 0 and 100 mg/dL level of ethanol. Therefore the test device so prepared is still not sufficiently sensitive to ethanol, o-dianisidine is believed to be an insufficiently sensitive indicator to provide a test device for 100 mg/dL ethanol which develops a colorimetric response in less than 5 minutes.

A similar lack of sensitivity was seen when a Phillips assay which follows the aldehyde produced by the action of alcohol oxidase on ethanol. Test devices were prepared by dipping Whatman 3 MM filter paper into Solution 1 or Solution 2, below. Each type was dried for 10 minutes at 60° C. in an air oven.

| | Solution 1 | Solution 2 |
|---|---|---|
| MBTH-HCl (0.04%) | 2.0 ml | 2.0 ml |
| AOD (500 IU/mL) | 0.05 ml | 1.0 ml |
| Ferric chloride (0.2% in 0.1 N HCl) | 8.0 ml | 7.0 ml |

In Solution 2, the concentration of alcohol oxidase was increased 20 times over that in Solution 1. Test devices prepared in either manner showed no reaction when contacted by an aqueous test sample containing 10 mg/dL ethanol. This result was not unexpected since the Phillips aldehyde based assay required one hour incubation of the ethanol with the assay solution, making it unsuitable for a rapid dip-and-read test.

B. False Positive Produced if Solution Assay Reagent Concentration Increased to Produce Sensitive Test Since it was believed that the insensitivity of the test device, produced in portion A, to 100 mg/dL of ethanol might be due to the indicator, o-dianisidine, used in solution assays, two further experiments were performed. In the first, (I), the concentrations of o-dianisidine and alcohol oxidase were increased further; in the second, (II), a more sensitive indicator, 3,3',5,5'-tetramethylbenzidine (TMB) was substituted.

| I. o-dianisidine.2HCl (0.1% in 0.1 M phosphate, pH 7.5) | 45 ml |
|---|---|
| POD, (12 mg/ml) | 0.5 ml |
| AOD (250 IU/ml) | 5.0 ml |
| II. first dip | |
| 0.05 M TMB | |
| Aerosol ® O.T. in toluene | |
| second dip | |
| 0.1 phosphate, pH 7.5 | 4.5 ml |
| POD (12 mg/ml) | 0.5 ml |
| AOD (500 IU/ml) | 1.0 ml |
| water | 4.0 ml |

Composition I was incorporated onto Whatman 3 MM paper by dipping. The paper immediately turned light brown, a color which should have been an indication of the presence of ethanol. The impregnated paper was dried 15 minutes at 60° in an air oven. The brown color continued to develop and become more intense with time. When the dried paper was contacted with an aqueous sample containing 100 mg/dL of ethanol, in less than 5 minutes the color was discernably different from the false positive color. Therefore, the strips exhibited sufficient sensitivity, but their false positive reaction made them unsuitable for use.

Composition II was incorporated into Whatman 3 MM paper by a two-step impregnation with drying in the air oven between impregnations. The paper was first dipped in the TMB, Aerosol ® O.T., toluene solution and dried 3 minutes at 60° C. After dipping in the second solution containing alcohol oxidase, the strips developed an intense blue color. The intensity of the color diminished somewhat on drying, but the dried doubly impregnated paper was still a pronounced blue-green. Although the strip exhibited a discernable color change in less than 5 minutes when contacted with an aqueous ample containing 100 mg/dL ethanol, the false positive color seen in uncontacted strips made the formulation unsuitable for use.

Both strip formulations also exhibited a small increase in color when contacted with water.

C. Single Chromogenic Component

Whatman 3 MM paper was incorporated with the test composition including an azide, peroxidase and 3,3',5,5'-tetramethylbenzidine (TMB) as the chromogenic indicator system. The chromogenic indicator, TMB, was incorporated first by dipping the paper into a solution of TMB in toluene containing 0.5% Aerosol ® OT. The paper was then dried in an air oven at 60° C. for 10 minutes.

The dried paper was then dipped into a solution containing:

| | |
|---|---|
| polyvinylpyrolidone (IC-30) 15% in water | 2.0 mL |
| Emulphor ® ON 870 5% in water | 2.0 mL |
| phosphate buffer 0.5 M, pH 8.5 | 2.0 mL |
| water | 2.25 mL |
| sodium azide, 0.03 M | 0.25 mL |
| POD, 12 mg/mL | 0.5 mL |
| AOD, 400 IU/mL | 1.0 mL |

The doubly incorporated paper was dried 15 minutes at 60° C. This paper exhibited no color (false positive) prior to contact with an ethanol containing sample.

A 0.5×0.5 cm piece of the doubly dried and incorporated paper was affixed to support member formed by an elongated piece of rigid nonreactive material such as polystyrene which will then act as a handle.

This formulation is the best mode known to the inventors for preparing a test device sensitive to at least 100 mg/dL ethanol in an aqueous test sample. The test device reacts with this sensitivity to provide a detectable colorimetric response in one to two minutes.

D. Test Device Without Azide

Whatman 31 ET paper was first dipped into a solution containing peroxidase, alcohol oxidase and one component of a coupled chromogenic indicator and dried 15 minutes at 60° C. in an air oven. The dried paper was then dipped in Solution 2 and dried 5 minutes at 60° C.

Solution 1

| | |
|---|---|
| POD (3 mg/mL in 1.0 M sodium phosphate, pH 7.5) | 4.0 mL |
| Emulphor ® ON 870, (5% in water) | 4.0 mL |
| AOD (850 IU/mL | 3.5 mL |
| DHSA (0.2 M in water) | 2.0 mL |
| water | 6.5 mL |

Solution 2
4-aminoantipyrine, 0.02M, in toluene

When a device is prepared without the addition of an azide, the paper exhibits a slight coloration. However, the components remain substantially in the reduced (uncolored) form in the final device, the device is sensitive to at least 100 mg/dL ethanol in an aqueous test sample and when contacted with such a sample, the device exhibits a detectable colorimetric response in one to two minutes. Such a device is particularly suitable for a presumptive test for ethanol wherein the presence of ethanol would be indicated by a strong "positive" color.

E. Separation of Chromogenic Components Plus Azide

Although a solid phase ethanol device can be prepared as shown in portion D, even when using coupled chromogenic indicators which can be separated for incorporation, it is preferred to include an azide.

What man 31 ET paper was dipped in Solution 1 which includes sodium azide and dried in an air oven 15 minutes at 50° C. The dried paper was then dipped in Solution 2 and dried. The doubly dried and incorporated paper can be cut and affixed to one end of a support member formed by an elongated plastic handle for convenient handling.

Solution 1

| | |
|---|---|
| polyvinyl pyrolidone (15% in water) | 2.0 mL |
| POD (12 mg/mL in 1.0 M sodium phosphate, pH 7.5) | 0.5 mL |
| Emulphor ® ON 870 (5% in water) | 2.0 mL |
| AOD (800 IU/mL) | 3.0 mL |
| DHSA (0.1 M) | 2.0 mL |
| sodium azide (0.02 M in water) | 0.5 mL |

Solution 2
0.02M MBTH base in toluene

Devices prepared in this manner exhibit essentially no coloration prior to contact with an ethanol containing sample and can be used for either a presumptive test or for quantitation of the ethanol present in the sample.

F. Polymer Film Carrier Matrix

A test device having the specified characteristics can also be prepared using a polymer film as the carrier matrix using the film formulation presented below:

| | |
|---|---|
| First layer | |
| Latex | 2.0 mL |
| TMB.2HCl | 157 mg |
| Avicel RC 591-F | 3 gm |
| Water | 8.0 mL |
| Second layer | |
| Phosphate, 0.5 M, pH 7.5 | 2.0 mL |
| POD, 10 mg/mL | 0.5 mL |
| Sodium azide, (8 mM) | 0.5 mL |
| Emulphor ® ON 870, (30%) | 1.0 mL |
| Latex | 2.0 mL |
| AOD, 500 IU/mL | 1.0 mL |
| Water | 3.0 mL |
| Avicel RC 591-F | 3.0 gm |

The latex is Polysar XE 465, a 60:40 styrene-butadiene copolymer containing 50% solids, obtained from Polysar Incorporated, Monaca, PA. Avicel RC 591-F is a microcrystalline cellulose obtained from FMC Corp., Food and Pharmaceutical Products Div., Philadelphia, PA.

The film is applied in two layers using a doctor blade. A preferred film thickness is about 30 to 40 microns giving a dry film thickness of about 25-35 microns. However, the thickness of the film is not critical to the performance of the device. The film can be aired dried or dried in the air oven at 60° C. for 10 minutes.

G. Phase Inversion Membranous Film as the Carrier Matrix

A solid state test device which is sensitive to at least 100 mg/dL ethanol and provides a colorimetric response in less than 5 minutes can also be prepared using phase inversion membraneous films.

A white hydrophilic membrane is prepared as follows:

With high speed stirring Solution 2 is slowly added (dropwise) to Solution 1. The "cloud point" will be reached upon completion of addition. To this add slowly with good stirring 2.0 grams Cab-o-sil.

Using a doctor blade case the material at 50 mL thickness on clear Trycite support member. Dry the film at 75° C. for 8-10 minutes.

| Solution 1 | |
| --- | --- |
| Cellulose acetate (viscosity 45) 15% plus 1.5% KP-140 in acetone | 36.0 gm |
| 15% SMA 2625A plus 1.5% KP-140 in acetone | 4.0 gm |
| Toluene | 2.0 mL |
| Solution 2 | |
| Sorbitol (60 %) | 1.8 mL |
| Sodium azide (0.03 M) | 1.8 mL |
| Emulphor ® ON 870 (10%) | 1.0 mL |
| POD (20 mg/dL) | 0.5 mL |
| AOD (500 IU/mL) | 1.8 mL |
| 2-propanol | 6.0 mL |
| Phosphate buffer, pH 7.5, 0.05 M | 11.2 mL |

Cellulose acetate (viscosity 45) can be obtained from Eastman Chemical Products, Inc., Kingsport, TN. KP-140 is tributoxyethylphosphate, a plasticizer, obtained from FMC Corp., Industrial Chemical Group, Philadephia, PA. SMA 262A is a styrene-maleic anhydride copolymer from Atlantic Richfield Co., Philadelphia, PA. Cab-o-sil is a fused silic polymer obtained from Cabot Corp., Boston, MA.

The completed white, hydrophilic membrane is then impregnated with a chromogenic indicator system. One impregnating solution would be 0.05M 3,3',5,5'-tetramethylbanzidine with 0.5% Aerosol® OT in toluene. Another impregnating solution would be 0.5% gum guaic in chloroform ($CHCl_3$). Either solution can be impregnated into the phase inverted film by roller application to the surface of the film at speeds of 10 to 50 feet per minute. The wetted films is then dried at the flash point of the solvent.

Although the invention has been described with a certain degree of particularity, it is understood that the present disclosure has been made only by way of example and that numerous changes in the details can be resorted to without departing from the scope of the invention.

What is claimed is:

1. A dry solid state reagent test device for determining ethanol in body fluids in concentrations as low as 100 mg/dL, capable of providing an analytical colorimetric response in less than 5 minutes, said device comprising:
   (a) a carrier matrix; and
   (b) a test composition incorporated into the carrier matrix, said test composition including
      (i) a chromogenic indicator system capable of providing a colorimetric response, wherein a chromogenic component of the indicator system is substantially in the reduced form;
      (ii) a peroxidatively active substance;
      (iii) from about 0.5 to about 5 mM alkali metal azide; and
      (iv) from about 20 to about 200 IU per milliliter alcohol oxidase.

2. The test device of claim 1 in which the chromogenic indicator system is a single indicator component.

3. The test device of claim 2 in which the test composition additionally includdds a buffer capable of providing a pH in the range of from about 5 to 9.

4. The test device of claim 3 in which the test composition additionally includes a shelf-like stabilizer.

5. A process for determining the presence of ethanol in an aqueous test sample, the process comprising contacting the test sample with the test device of claim 1 and observing in less than 5 minutes any detectable colorimetric response associated with the presence of ethanol.

6. A method for the manufacture of a dry solid state reagent strip for determining ethanol in body fluids in concentrations as low as 100 mg/dL anc capable of providing an anlytical, colorimetric response in less than 5 minutes, said method comprising the steps of:
   (a) preparing a first mixture of a single component chromogenic indicator and an organic solvent;
   (b) preparing an aqueous second mixture of a peroxidatively active substance, any remaining components of the chromogenic indicator system, from about 0.5 to about 5 mM alkali metal azide and from about 20 to about 200 IU per milliliter alcohol oxidase;
   (c) incorporating the carrier matrix with one of the first or second mixtures and drying; and
   (d) incorporating the carrier with the other of the first or second mixtures and drying.

* * * * *